US012605426B2

(12) United States Patent
Na et al.

(10) Patent No.: US 12,605,426 B2
(45) Date of Patent: Apr. 21, 2026

(54) PHARMACEUTICAL COMPRISING SUSTAINED-RELEASE MICROSPHERES INCLUDING GLP-1 ANALOGUE OR PHARMACEUTICALLY ACCEPTABLE SALT THEREOF

(71) Applicant: G2GBIO, INC., Daejeon (KR)

(72) Inventors: Yongha Na, Daejeon (KR); Dongpil Won, Daejeon (KR); Yejin Kim, Daejeon (KR); Juhan Lee, Daejeon (KR); Heekyoung Choe, Ansan-si (KR); Eunyoung Seol, Sejong (KR); Heeyong Lee, Daejeon (KR)

(73) Assignee: G2GBIO, INC., Daejeon (KR)

( * ) Notice: Subject to any disclaimer, the term of this patent is extended or adjusted under 35 U.S.C. 154(b) by 817 days.

(21) Appl. No.: 17/904,133

(22) PCT Filed: Feb. 15, 2021

(86) PCT No.: PCT/KR2021/001928
§ 371 (c)(1),
(2) Date: Aug. 12, 2022

(87) PCT Pub. No.: WO2021/162532
PCT Pub. Date: Aug. 19, 2021

(65) Prior Publication Data
US 2023/0096928 A1     Mar. 30, 2023

(30) Foreign Application Priority Data
Feb. 14, 2020     (KR) ........................ 10-2020-0018640

(51) Int. Cl.
| | | |
|---|---|---|
| *A61K 38/26* | (2006.01) |
| *A61K 9/00* | (2006.01) |
| *A61K 9/16* | (2006.01) |
| *A61K 47/12* | (2006.01) |
| *A61K 47/34* | (2017.01) |
| *A61P 3/04* | (2006.01) |
| *A61P 3/06* | (2006.01) |
| *A61P 9/10* | (2006.01) |
| *A61P 25/28* | (2006.01) |

(52) U.S. Cl.
CPC ........... *A61K 38/26* (2013.01); *A61K 9/0019* (2013.01); *A61K 9/16* (2013.01); *A61K 9/1641* (2013.01); *A61K 9/1647* (2013.01); *A61K 9/1694* (2013.01); *A61K 47/12* (2013.01); *A61K 47/34* (2013.01); *A61P 3/04* (2018.01); *A61P 3/06* (2018.01); *A61P 9/10* (2018.01); *A61P 25/28* (2018.01)

(58) Field of Classification Search
None
See application file for complete search history.

(56) References Cited

U.S. PATENT DOCUMENTS

| | | | | |
|---|---|---|---|---|
| 9,265,835 | B2 * | 2/2016 | Li | ........................... A61K 47/34 |
| 9,764,003 | B2 | 9/2017 | Jensen | |
| 2005/0142205 | A1 | 6/2005 | Rashba-Step et al. | |
| 2014/0004198 | A1 | 1/2014 | Balschmidt et al. | |
| 2019/0350870 | A1 | 11/2019 | Farokhzad et al. | |
| 2020/0113836 | A1 * | 4/2020 | Bae | ......................... A61K 9/107 |

FOREIGN PATENT DOCUMENTS

| | | | |
|---|---|---|---|
| AU | 2018271381 | 6/2019 | |
| CN | 102940609 | 2/2013 | |
| CN | 105126082 | 12/2015 | |
| CN | 105878191 | 8/2016 | |
| CN | 106924750 | 7/2017 | |
| CN | 107929718 | 4/2018 | |
| CN | 108606957 | 10/2018 | |
| CN | 110101846 | 8/2019 | |
| CN | 110101846 A | * 8/2019 | ........... A61K 9/5031 |
| CN | 110623944 | 12/2019 | |
| CN | 110709067 | 1/2020 | |
| EP | 4005587 | 6/2022 | |
| JP | 2013-525471 | 6/2013 | |
| JP | 2016-515612 | 5/2016 | |
| JP | 6356660 | 7/2018 | |
| KR | 10-0466637 | 1/2005 | |
| KR | 10-2008-0094616 | 10/2008 | |
| KR | 10-1411349 | 6/2014 | |

(Continued)

OTHER PUBLICATIONS

Espacenet machine translation of CN110101846A, Sun, Yanhua et al., published Aug. 9, 2019 (Year: 2019).*
Cecil Textbook of Medicine, 20th edition, vol. 2, Edited by J. Claude Bennett, "Alzheimer's disease and related demtnias" (Year: 1996).*
Definition of "prevent", WordNet Search 3.1, obtained 2021 (Year: 2021).*
Maczurek et al., Advanced Drug Delivery Reviews, "Lipoic acid as an anti-inflammatory and neuroprotective treatment for Alzheimer's disease", 2008, vol. 60, pp. 1463-1470 (Year: 2008).*
"Biodegradable polymers for controlled release" , Resomer®—Evonik Industries, https://healthcare.evonik.com/en/drugdelivery/parenteral-drug-delivery/parenteral-excipients/bioresorbable-polymers/standard-polymers.

(Continued)

*Primary Examiner* — Bahar Craigo
(74) *Attorney, Agent, or Firm* — LEX IP MEISTER, PLLC

(57) ABSTRACT

The present invention relates to a pharmaceutical composition useful for prevention or treatment of diabetes, beta-cell function preservation, high blood pressure, hyperlipidemia, obesity, non-alcoholic steatohepatitis or neurodegenerative diseases such as Alzheimer's disease and Parkinson's disease, as it comprises a sustained-release microsphere comprising semaglutide, a pharmaceutically acceptable salt, hydrate or solvate thereof, and thereby, it can effectively inhibit fatal side-effects by preventing initial burst of a drug and comprise a high content of drug compared to a particle size, and therefore, it can minimize the patient's pain and inflammatory reaction that may occur during administration.

6 Claims, 5 Drawing Sheets

(56) References Cited

FOREIGN PATENT DOCUMENTS

| KR | 10-2014-0138873 | 12/2014 |
| KR | 10-2016-0002945 | 1/2016 |
| KR | 10-1925620 | 12/2018 |
| KR | 10-2019-0064509 | 6/2019 |
| KR | 10-2019-0064526 | 6/2019 |
| KR | 10-2019-0101408 | 8/2019 |
| KR | 10-2047983 | 11/2019 |
| KR | 10-2020-0009689 | 1/2020 |
| KR | 10-2020-0100392 | 8/2020 |
| WO | 2006097537 | 9/2006 |
| WO | 2013-108035 | 7/2013 |
| WO | 2013189988 | 12/2013 |
| WO | 2017-186073 | 11/2017 |
| WO | 2017-186076 | 11/2017 |
| WO | 2017186075 | 11/2017 |
| WO | 2018-136909 | 7/2018 |
| WO | 2018-221884 | 12/2018 |
| WO | 2019038412 | 2/2019 |
| WO | 2019072941 | 4/2019 |
| WO | 2019-108030 | 6/2019 |
| WO | 2019149880 | 8/2019 |
| WO | 2019215063 | 11/2019 |
| WO | 2020028907 | 2/2020 |

OTHER PUBLICATIONS

KIPO, PCT Search Report & Written Opinion of PCT/KR2021/001928 dated Jun. 15, 2021.

Zolnik, Banu S. et al., "Effect of acidic pH on PLGA microsphere degradation and release", Journal of Controlled Release, 2007, pp. 338-344.

Banu S. Zolnik et al., "Effect of acidic pH on PLGA microsphere degradation and release", Journal of Controlled Release 122 (2007) 338-344, Jun. 5, 2007.

EPO, Search Report of EP 21754621.7 dated Mar. 18, 2024.

Christoph Kapitza et al., "Effects of semaglutide on beta cell function and glycaemic control in participants with type 2 diabetes: a randomized, double-blind, placebo-controlled trial", Diabetologia, 2017, vol. 60, pp. 1390-1399, May 19, 2017.

Philip Newsome et al., "Effect of semaglutide on liver enzymes and markers of inflammation in subjects with type 2 diabetes and/or obesity", Alimentary pharmacology & therapeutics, 2019, vol. 50, pp. 193-203, Jun. 10, 2019.

Maddalena Grieco et al., "Glucagon-Like Peptide-1: A Focus on Neurodegenerative Diseases", Frontiers in Neuroscience, 2019, vol. 13, N.1112, pp. 1-7, Oct. 18, 2019.

Rospatent, Ofice Action of the corresponding RU Patent Application No. 2022122081., dated May 17, 2024, total 34 pages.

Hiroaki Okada, "Biodegradable Long-Term Sustained Release Injections", Journal of Pharmaceutical Science and Technology, Japan, 2008, vol. 68, Issue 2, pp. 136-142, Released on J-STAGE Mar. 31, 2019, Online ISSN 2188-3149, Print ISSN 0372-7629.

JPO, Office Action of JP 2022-548939 dated Jul. 18, 2023.

Merck Resomer® RG 503, Poly(D,L-lactide-co-glycolide) Product Introduction Page, Resomer RG 503, Poly (D,L-lactide-co-glycolide) lactide glycolide 50 50, ester terminated, Mw 24,000-38,000 26780-50-7 (sigmaaldrich.com).

IP Australia, Office Action of the corresponding AU Patent Application No. 2021219556, dated Nov. 30, 2023.

* cited by examiner

[FIG. 1]
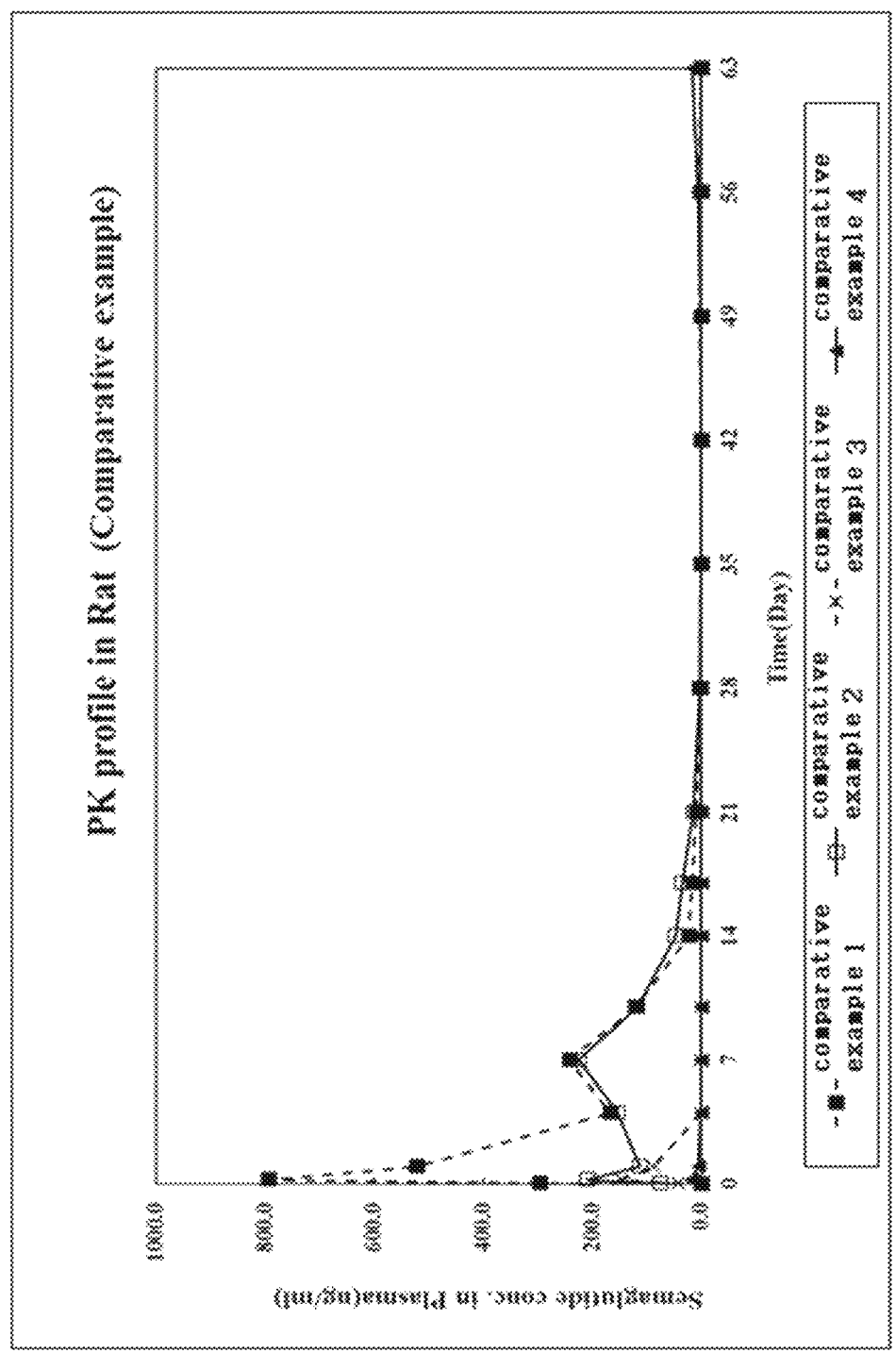
PK profile in Rat (Comparative example)

[FIG.2]
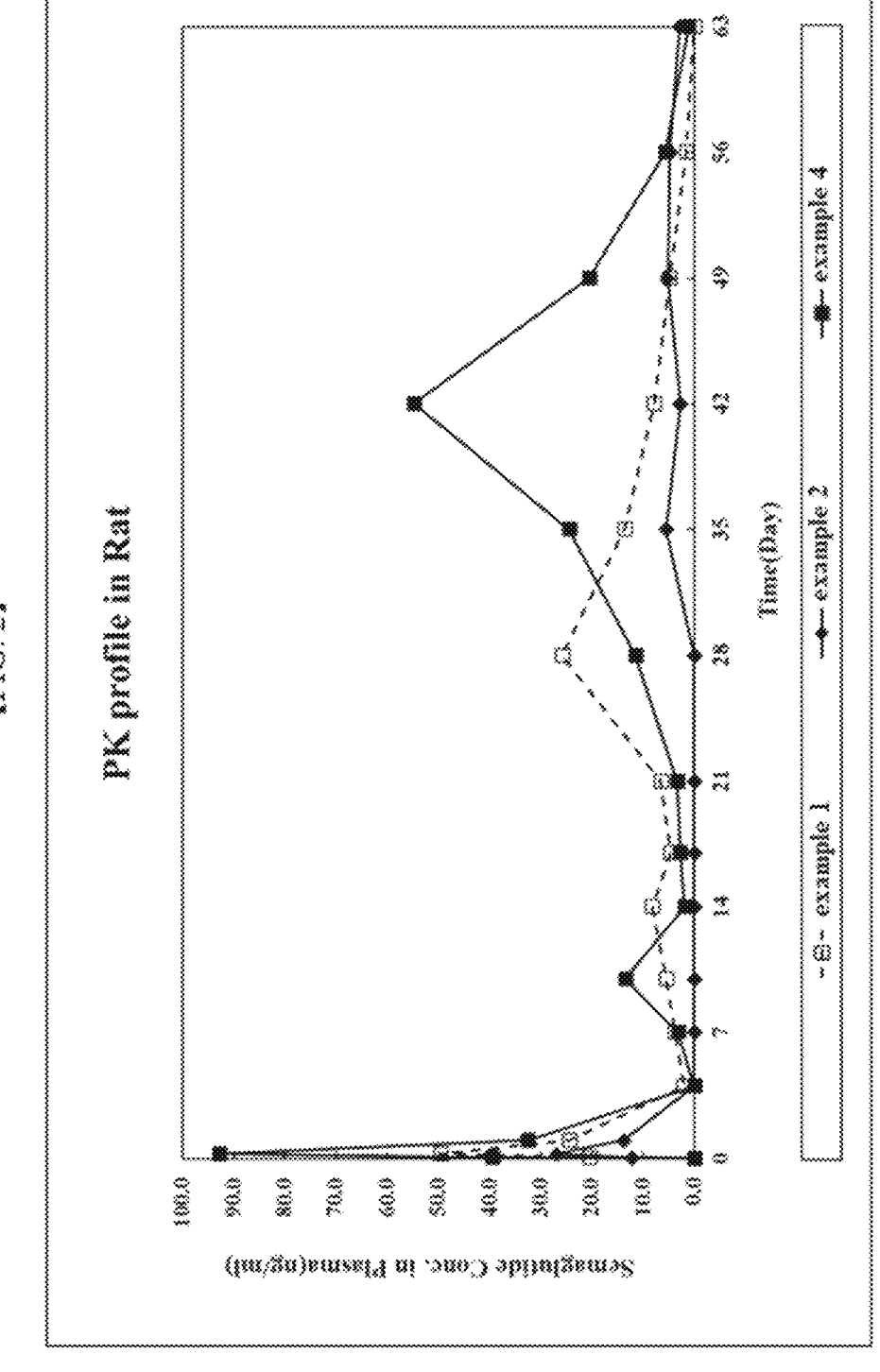
PK profile in Rat

[FIG. 3]
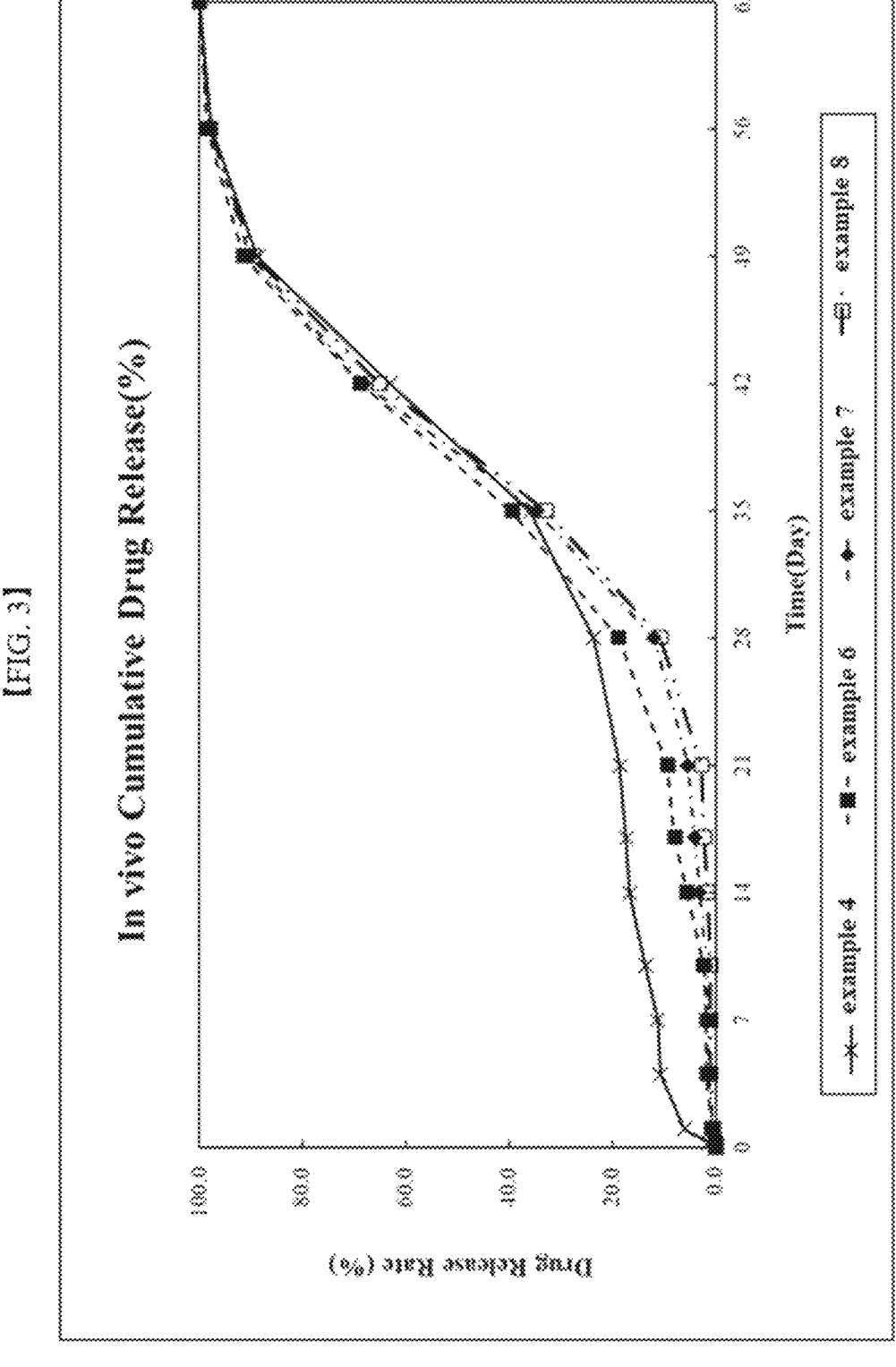

[FIG.4]
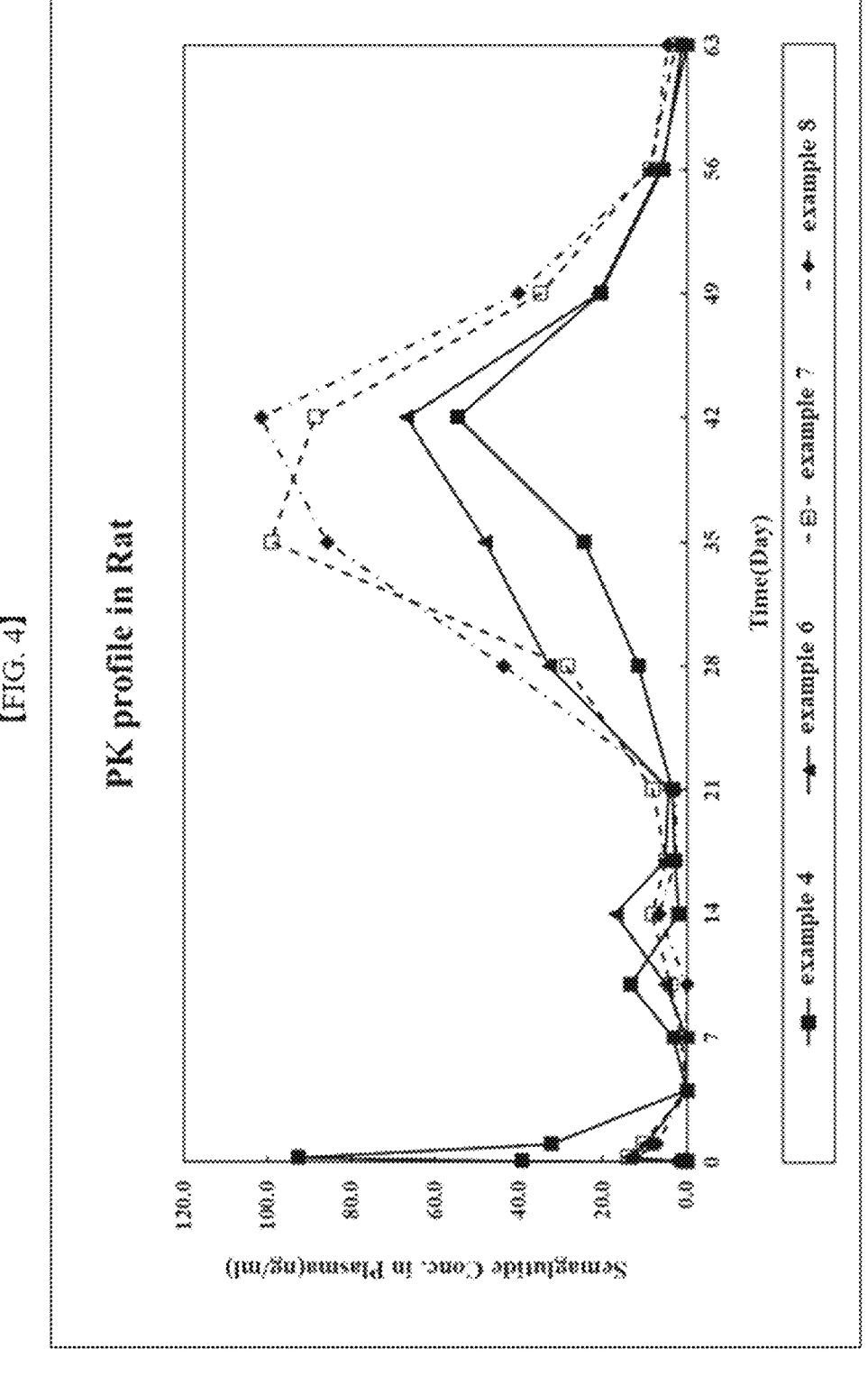
PK profile in Rat

【FIG. 5】
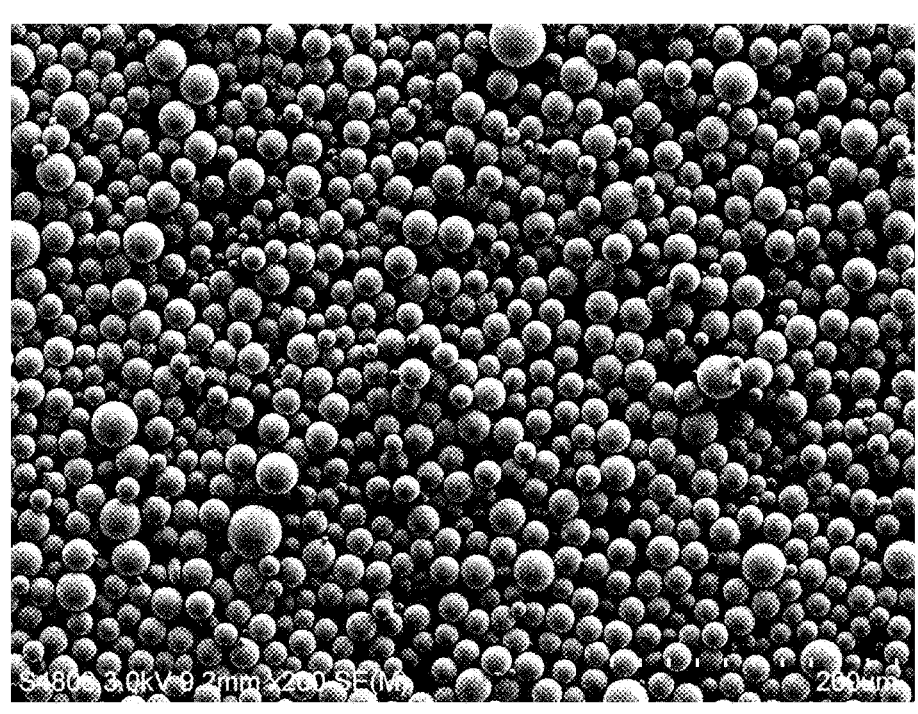

PHARMACEUTICAL COMPRISING SUSTAINED-RELEASE MICROSPHERES INCLUDING GLP-1 ANALOGUE OR PHARMACEUTICALLY ACCEPTABLE SALT THEREOF

TECHNICAL FIELD

The present invention relates to a pharmaceutical composition comprising a sustained-release microsphere comprising a GLP-1 analogue or a pharmaceutically acceptable salt thereof, and a method for preparation of the sustained-release microsphere.

BACKGROUND ART

Glucagon-like peptide-1 (GLP-1) is derived from pre-pro glucagon, a 158 amino acid precursor polypeptide that is processed in different tissues, and forms numerous different proglucagon-induced peptides, including glucagon, glucagon-like peptide-1 (GLP-1), glucagon-like peptide-2 (GLP-2) and oxyntomodulin (OXM), which are involved in various physiological functions including glucose homeostasis, insulin secretion, gastric emptying, intestinal growth and regulation of food intake. GLP-1 is produced as a 37-amino acid peptide corresponding to amino acids 72~108 (prepro-glucagon 92~128) of proglucagon. GLP-1 (7-36) amide or GLP-1 (7-37) acid is a biologically active form of GLP-1 that exhibits essentially equivalent activity in a GLP-1 receptor. It has been discovered that GLP-1 and GLP-1 analogues acting as an agonist in the GLP-1 receptor for example, provide effective glycemic control for treating a patient of type 2 diabetes, a body weight loss effect, beta-cell function preservation, alleviation of high blood pressure and hypoglycemia and/or hyperlipidemia. Specific GLP-1 analogues, including Byetta® & Bydureon BCise® (exenatide), Ozempic® (semaglutide), Victoza® (liraglutide), Adlyxin® (lixisenatide); Tanzeum® (albiglutide), and Trulicity® (dulaglutide), are commercially available or in development.

GLP-1 agonists, such as semaglutide, are peptides and administration of these peptides is frequently conducted by injection due to various barriers such as enzymatic degradation in the gastrointestinal tract and intestinal mucosa, insufficient absorption from the intestinal mucosa, and first pass metabolism in liver. And recently oral administrative agents have also been commercialized, but the bioavailability is very low compared to injection, so the dosage is significantly high. Furthermore, a preparation comprising semaglutide is formulated in a form of direct administration (self-administration) for continuous management of obesity or diabetes, so it is very important to manage pain, inflammatory reaction, and the like that may occur at the site of administration.

On the other hand, for long-term elution of a peptide such as the GLP-1 agonist, a technique for encapsulating peptide in microspheres is known, but in order to exhibit an effective long-term pharmacological effect, a high content of peptide should be included in the microsphere. However, in this case, an initial burst of a drug inevitably occurs, and in particular, the GLP-1 agonist has a problem that may cause fatal side-effects due to this initial burst.

DISCLOSURE

Technical Problem

The present invention has been proposed to solve the above problems, and an object of the present invention is to provide a pharmaceutical composition comprising a sustained-release microsphere comprising semaglutide, a pharmaceutically acceptable salt, hydrate or solvate thereof, which prevents initial excessive drug release of semaglutide, and shows properties of long-term sustained drug release, and a method for preparation of the sustained-release microsphere.

Technical Solution

In order to achieve the above objects, the present invention provides a pharmaceutical composition which comprises biodegradable polymer, and comprises a semaglutide sustained-release microsphere having a semaglutide content of 3% by weight or more, based on the total microsphere weight, as one aspect.

As another aspect, the biodegradable polymer may be one or more selected from the group consisting of a polymer selected from the group consisting of polylactide (PLA), polyglycolide (PGA), polylactide-co-glycolide (PLGA) which is a copolymer of lactide and glycolide, polyorthoester, polyanhydride, polyhydroxybutyric acid, polycaprolactone and polyalkylcarbonate; a copolymer or simple mixture of 2 or more thereof; a copolymer of the polymer and polyethyleneglycol (PEG); and a polymer-sugar complex which the polymer or copolymer is linked with sugar.

As other one aspect, the pharmaceutically acceptable salt of semaglutide may be acetate, benzoate, hydroxynaphthoate, napadisylate or pamoate.

As other one aspect, the intrinsic viscosity of polylactide-co-glycolide or polylactide among the biodegradable polymers may be 0.16~1.7 dL/g.

As other one aspect, the average particle size of the microsphere containing the semaglutide or pharmaceutically acceptable salt thereof may be 5 μm to 100 μm.

As other one aspect, the span value of the microsphere containing the semaglutide or pharmaceutically acceptable salt thereof may be 1.2 or less.

As other one aspect, the weight of the microsphere containing the semaglutide or pharmaceutically acceptable salt thereof may be 20 to 1000 mg, 20 mg to 800 mg, 20 mg to 600 mg, 20 mg to 500 mg, 30 mg to 1000 mg, 30 mg to 800 mg, 30 mg to 600 mg, 30 mg to 500 mg, 40 mg to 1000 mg, 40 mg to 800 mg, 40 mg to 600 mg, 40 mg to 500 mg, 50 mg to 1000 mg, 50 mg to 800 mg, 50 mg to 600 mg, or 50 mg to 500 mg.

As other one aspect, the microsphere may comprises one or more release controlling agents selected from the group consisting of butyric acid, valeric acid, caproic acid, enantic acid, caprylic acid, pelargonic acid, capric acid, undecylic acid, lauric acid, tridecylic acid, myristic acid, pentadecylic acid, palmitic acid, heptadecylic acid, stearic acid, nonadecylic acid, arachidic acid, isocrotonic acid, oleic acid, elaidic acid, sorbic acid, linoleic acid, arachidonic acid, hydroxynaphthoic acid, napadisylic acid and pamoic acid.

As other one aspect, the present invention provides a method for preparation of a sustained-release microsphere containing semaglutide or a pharmaceutically acceptable salt thereof, comprising the following steps:

(a) dissolving semaglutide or a pharmaceutically acceptable salt thereof and biodegradable polymer in an organic solvent to prepare solution (dispersed phase) containing the semaglutide or pharmaceutically acceptable salt thereof and the biodegradable polymer;

(b) adding the solution containing the semaglutide or pharmaceutically acceptable salt thereof and the polymer prepared in the step (a) to an aqueous phase (continuous phase) containing a surfactant to prepare emulsion;

(c) extracting and evaporating an organic solvent from the dispersed phase in an emulsion state prepared in the step (b) to the continuous phase to form a microsphere; and (d) collecting the microsphere from the continuous phase of the step (c) to prepare a microsphere comprising semaglutide or pharmaceutically acceptable salt thereof.

As other one aspect, the biodegradable polymer may be a mixture of 2 or more biodegradable polymers different each other.

As other one aspect, the present invention provides a method for preparation of a sustained-release microsphere containing semaglutide or pharmaceutically acceptable salt thereof, comprising the following steps:

(a') dissolving semaglutide or a pharmaceutically acceptable salt thereof and 2 or more biodegradable polymers different each other in an organic solvent to prepare a solution (dispersed phase) containing the semaglutide or pharmaceutically acceptable salt thereof and the polymer;

(b') adding the solution containing the semaglutide or pharmaceutically acceptable salt thereof and the polymer prepared in the step (a') to an aqueous phase (continuous phase) containing a surfactant to prepare emulsion;

(c') extracting and evaporating an organic solvent from the dispersed phase in an emulsion state prepared in the step (b') to the continuous phase to form a microsphere; and (d') repeating a process for preparing a microsphere comprising collecting a microsphere from the continuous phase in the step (c') to prepare a microsphere 2 times or more to prepare 2 or more microspheres different each other, (e') mixing the 2 or more microspheres consisting of different kinds of polymers each other.

As other one aspect, the present invention provides a method for preparation of a sustained-release microsphere containing semaglutide or a pharmaceutically acceptable salt thereof, comprising the following steps:

(a'') dissolving semaglutide or a pharmaceutically acceptable salt thereof and 2 or more biodegradable polymers different each other in an organic solvent, respectively, to prepare 2 or more solutions (dispersed phase) containing the semaglutide or pharmaceutically acceptable salt thereof and the polymer;

(b'') adding the 2 or more solutions containing the semaglutide or pharmaceutically acceptable salt thereof and polymer prepared in the step (a'') to an aqueous phase (continuous phase) containing a surfactant, respectively, to prepare 2 or more emulsions;

(c'') extracting and evaporating an organic solvent from the 2 or more the dispersed phase in an emulsion state prepared in the step (b'') to the continuous phase, by putting the 2 or more the dispersed phase in emulsion state prepared in the step (b'') into the same reactor, to form microspheres; and (d'') collecting microspheres from the continuous phase in the step (c'').

As other one aspect, the pH of the continuous phase used in the methods for preparation may be 5 or less.

Advantageous Effects

The sustained-release pharmaceutical composition comprising semaglutide, a pharmaceutically acceptable salt, hydrate or solvate thereof according to one preparative example of the present invention can effectively inhibit fatal side-effects by preventing initial burst of a drug, and can comprise a high content of drug compared to a particle size, and therefore, it has an effect capable of minimizing the patient's pain and inflammatory reaction that may occur during administration.

DESCRIPTION OF DRAWINGS

FIG. 1 is a graph confirming the change in plasma drug concentration over time after administering microspheres comprising semaglutide prepared in Comparative examples 1 to 4 into a rat.

FIG. 2 is a graph confirming the change in plasma drug concentration over time after administering microspheres comprising semaglutide prepared in Example 1, Example 2 and Example 4 into a rat.

FIG. 3 is a graph confirming the change in cumulative release of the drug over time after administering microspheres comprising semaglutide prepared in Example 4, Example 6, Example 7 and Example 8 into a rat.

FIG. 4 is a graph confirming the change in plasma drug concentration over time after administering microspheres comprising semaglutide prepared in Example 4, Example 6, Example 7 and Example 8 into a rat.

FIG. 5 is a photograph showing the result of performing morphological analysis using an electron microscope for the microsphere prepared according to Example 4.

BEST MODE

Hereinafter, the present invention will be described in detail.

The present invention comprises semaglutide or a pharmaceutically acceptable salt thereof as an active ingredient.

Semaglutide is GLP-1 receptor agonist $N^{6.26}$-{18-[N-(17-carboxy-heptadecanoyl)-L-$\gamma$-glutamyl]-10-oxo3,6,12,15-tetraoxa-9,18-diazaoctadecanoyl}-[8-(2-amino-2-propanoic acid), 34-L-arginine]human glucagon-like peptide 1(7-37), and is also called N-epsilon26-[2-(2-{2-[2-(2-{2-[(S)-4-carboxy-4-(17-carboxyheptadecanoylamino)butyrylamino] ethoxy}ethoxy)acetylamino]ethoxy}ethoxy)acetyl][Aib8, Arg34]GLP-1-(7-37). The structure of the semaglutide is as shown in Chemical formula 1 below.

[Chemical formula 1]

-continued

15

This semaglutide may be prepared as described in Preparative example 4 of International Patent Publication WO2006/097537, and commercially available semaglutide may be used.

Semaglutide may be present particularly in a form of pharmaceutically acceptable salt. As the salt, salts commonly used in the art may be used without limitation. The term of the present invention, "pharmaceutically acceptable salt" means any of all organic or inorganic addition salts of the compound in which side effects due to these salts do not reduce beneficial efficacy of an active ingredient at a concentration having an effective action that is relatively nontoxic and harmless. A specific example may include acetate, benzoate, hydroxynaphthoate, nafadisylate or pamoate of semaglutide, or the like, but not limited thereto.

The active ingredient of the present invention, the semaglutide or pharmaceutically acceptable salt thereof may be in various forms, for example, in an amorphous or crystalline form.

The biodegradable polymer comprised in the semaglutide sustained-release microsphere comprised in the pharmaceutical composition according to the present invention is selected from the group consisting of a polymer selected from the group consisting of polylactide (PLA), polyglycolide (PGA), polylactide-co-glycolide (PLGA) which is a copolymer of lactide and glycolide, polyorthoester, polyanhydride, polyhydroxybutyric acid, polycaprolactone and polyalkylcarbonate, a copolymer or simple mixture of 2 or more, a copolymer of the polymer and polyethyleneglycol (PEG), and a polymer-sugar complex which the polymer or copolymer is linked with sugar. As one specific aspect, the pharmaceutical composition according to the present invention may comprise a microsphere comprising 2 or more the biodegradable polymers. As another specific aspect, the pharmaceutical composition according to the present invention may comprise 2 or more microspheres comprising one or more polymers selected from the biodegradable polymer, respectively.

The 2 or more polymers selected from the group consisting of poly-lactide-co-glycolide and polylactide polymers, are not limited thereto, but the molar ratio of the lactide to glycolide in the copolymer may be 50:50 to 100:0, 60:40 to 90:10, or 70:30 to 80:20, and the intrinsic viscosity of the polymer is 0.16 dL/g to 1.7 dL/g, 0.2 dL/g to 1.3 dL/g, or 0.24 dL/g to 1.2 dL/g.

The intrinsic viscosity of the poly-lactide-co-glycolide or polylactide used in the present invention refers to one measured at a concentration of 0.1% (w/v) in chloroform at 25° C. using an Ubbelohde viscometer. When the intrinsic viscosity of poly-lactide-co-glycolide or polylactide is less than 0.16 dL/g, the molecular weight of the polymer is insufficient, and therefore, it is difficult to exhibit a sustained-release effect of semaglutide or a pharmaceutically acceptable salt thereof, and when the intrinsic viscosity is over 1.7 dL/g, an effect of delaying the release of semaglutide or a pharmaceutically acceptable salt thereof too much may occur. In addition, when manufacturing a microsphere using a polymer with high intrinsic viscosity, there is a problem in that an excessive amount of a manufacturing solvent should be used due to the high viscosity of the polymer, and it is difficult to manufacture reproducible microspheres. An example of the commercially available polymer having the aforementioned characteristics, may include RG502H, RG503H, RG504H, RG502, RG503, RG504, RG653H, RG752H, RG752S, RG755S, RG750S, RG757S, RG858S, R202H, R203H, R205H, R202S, R203S, R205S, R206S and R207S, which are Resomer series of Evonik company, and PDL 02A, PDL 02, PDL 04, PDL 05, PDLG 7502A, PDLG 7502, PDLG 7507, PDLG 5002A, PDLG 5002, PDLG 5004A and PDLG 5004 of Corbion company, and the like.

The content of the semaglutide or pharmaceutically acceptable salt thereof in the sustained-release microsphere containing the semaglutide or a pharmaceutically acceptable salt thereof according to the present invention is preferably 3% by weight or more, 3.5% by weight or more, 3.9% by weight or more as semaglutide based on the total weight of the microsphere. When the content of the semaglutide or pharmaceutically acceptable salt thereof in the microsphere is less than 3% by weight based on semaglutide, as the amount of the polymer used is too many compared to the drug, the bioavailability of the semaglutide or pharmaceutically acceptable salt thereof may be lowered, and when the content is excessively high, it is not preferable, since there is a problem of high initial release of the semaglutide or pharmaceutically acceptable salt thereof.

The microsphere containing the semaglutide or a pharmaceutically acceptable salt thereof according to the present invention may preferably have the uniform particle distribution of the average particle size of 5 μm to 100 μm, 5 to 90 μm, 5 μm to 80 μm, 10 μm to 90 μm, 10 μm to 80 μm, 15 μm to 100 μm, 15 μm to 90 μm, 15 μm to 80 μm, 70 μm to 100 μm, 70 μm to 90 μm, 70 μm to 80 μm, 60 μm to 100 μm, 60 μm to 80 μm, 60 μm to 70 μm, 90 μm to 100 μm, 20 μm to 90 μm, 20 μm to 70 μm, 20 μm to 60 μm, 30 μm to 80 μm, 30 μm to 60 μm, 40 μm to 70 μm, 40 μm to 50 μm, 30 μm to 40 μm, 20 μm to 30 μm, 5 μm to 30 μm, 5 μm to 20 μm, 10 μm to 20 μm, or 5 μm to 10 μm. The term used in the present invention, "average particle size" is a particle size corresponding to 50% of volume % in a particle size distribution curve, and means a median diameter, and expressed as D50 or D(v, 0.5).

When the average particle size of the microsphere containing the semaglutide or pharmaceutically acceptable salt thereof is less than 5 μm, it is not preferable as the release of a drug of the semaglutide or pharmaceutically acceptable salt thereof is too fast. When the average particle size is over 100 μm, it is not preferable, since a needle becomes too thick when administered to a human body, and therefore, it may cause symptoms during injection or the drug may leak into the injection site after injection.

The microsphere containing the semaglutide or pharmaceutically acceptable salt thereof of the present invention preferably has uniform particle distribution. The microsphere containing the semaglutide or pharmaceutically acceptable salt thereof having uniform particle distribution has less variation during injection than a non-uniform microsphere, and can be administered in a more accurate amount. It is preferable that the size distribution or span value of the microsphere containing the semaglutide or pharmaceutically acceptable salt thereof of the present invention is 1.5 or less. More preferably, it is preferable that the size distribution is 1.2 or less. More specifically, the size distribution or span value may be 1.5 or less, 1.2 or less, 0.1 to 1.5, 0.3 to 1.5, 0.5 to 1.5, 0.1 to 1.0, 0.4 to 1.0, 0.6 to 1.0, 0.2 to 0.8, or 0.4 to 0.8. The term used in the present invention, "size distribution" or "span value" is an index indicating uniformity of the particle size of the microsphere, and means a value obtained by the formula of Span value=(Dv0.9−Dv0.1)/Dv0.5. Herein, Dv0.1 is a particle size corresponding to 10% of volume % in a particle size distribution curve of the microsphere, and Dv0.5 is a particle size corresponding to 50% of volume % in a particle size distribution curve of the microsphere, and Dv0.9 means a particle size corresponding to 90% of volume % in a particle size distribution curve of the microsphere.

The sustained-release microsphere containing the semaglutide or pharmaceutically acceptable salt thereof of the present invention is administered by an injection route, for example, subcutaneous injection, and in particular, as it is possible to be self-administered, it is preferable that semaglutide is released in a relatively long period. Preferably, the sustained-release microsphere of the pharmaceutical composition according to the present invention is not limited thereto, but may release the semaglutide or pharmaceutically acceptable salt thereof for one month or more, 2 months or more, 3 months or more, 1 month to 2 months, 1 month to 3 months, 1 month to 4 months, 1 month to 5 months, 1 month to 6 months, 2 months to 6 months, 2 months to 5 months, 2 months to 4 months, 2 months to 3 months, 3 months to 5 months, or 3 months to 4 months. In addition, in the sustained-release microsphere containing the semaglutide or pharmaceutically acceptable salt thereof of the present invention, this release aspect is not particularly limited, but it is preferable that the semaglutide or pharmaceutically acceptable salt thereof is released by less than 10%, less than 15% or less than 20% within 24 hours, when administered in a living body.

In addition, in the pharmaceutical composition of the present invention, the total amount of the sustained-release microsphere comprising the semaglutide or pharmaceutically acceptable salt thereof may be 20 to 1000 mg, 20 mg to 800 mg, 20 mg to 600 mg, 20 mg to 500 mg, 30 mg to 1000 mg, 30 mg to 800 mg, 30 mg to 600 mg, 30 mg to 500 mg, 40 mg to 1000 mg, 40 mg to 800 mg, 40 mg to 600 mg, 40 mg to 500 mg, 50 mg to 1000 mg, 50 mg to 800 mg, 50 mg to 600 mg, or 50 mg to 500 mg. By comprising the sustained-release microsphere comprising the semaglutide or pharmaceutically acceptable salt thereof in the composition within the range, the composition according to the present invention has an advantage of not only minimizing the inflammatory reaction at the site of administration, but also allowing self-administration of a patient.

The microsphere comprising the semaglutide or pharmaceutically acceptable salt thereof comprised in the composition of the present invention may further comprise a release controlling agent. A substance used as the release controlling agent may include one or more selected from butyric acid, valeric acid, caproic acid, enantic acid, caprylic acid, pelargonic acid, capric acid, undecylic acid, lauric acid, tridecylic acid, myristic acid, pentadecylic acid, palmitic acid, heptadecylic acid, stearic acid, nonadecylic acid, arachidic acid, isocrotonic acid, oleic acid, elaidic acid, sorbic acid, linoleic acid, arachidonic acid, benzoate, hydroxynaphthoic acid, napadisylic acid and pamoic acid as an example, but not limited thereto. Preferably, the release controlling agent may be hydroxynaphthoic acid, napadisylic acid or pamoic acid, but not limited thereto.

The pharmaceutical composition comprising the microsphere comprising the semaglutide or pharmaceutically acceptable salt thereof according to the present invention may be formulated as various types of preparations, and for example, it may be a known formulation of a parenteral administration preparation. Accordingly, the pharmaceutical composition according to the present invention may further comprise a thickener, a stabilizer, a tonicifying agent, a pH adjusting agent, a surfactant, an excipient and/or a carrier in addition to the semaglutide or pharmaceutically acceptable salt thereof. The available tonicifying agent may include an aqueous excipient such as mannitol, sucrose, sorbitol, trehalose, lactose, sodium chloride, and the like or a saccharide, and the thickener may include sodium carmellose, sodium carboxymethyl cellulose, povidone, and the like as an example. As the surfactant, polyvinylalcohol, and the like are possible. In addition, as the buffer, sodium monohydrogen phosphate, citric acid anhydride, sodium hydroxide, sodium chloride, and the like may be used.

The pharmaceutical composition according to the present invention may be administered in a therapeutically effective dose of semaglutide, for example, in an effective dose in order to treat diabetes, specifically, type 2 diabetes, beta-cell function preservation, high blood pressure, hyperlipidemia, obesity, non-alcoholic steatohepatitis, or neurodegenerative diseases such as Alzheimer's disease and Parkinson's disease. The therapeutically effective dose of semaglutide may be evaluated by a doctor. The pharmaceutical composition comprising semaglutide according to the present invention may be administered once a month to once a quarter. In some specific examples, the one-month dosage of the composition according to the present invention may be 1.0 mg to 100 mg, 1.0 mg to 80 mg, 1.0 mg to 30 mg, 1.0 mg to 20 mg, 2.0 mg to 100 mg, 2.0 mg to 80 mg, 2.0 mg to 30 mg, 2.0 mg to 20 mg, 4.0 mg to 100 mg, 4.0 mg to 80 mg, 4.0 mg to 30 mg, 4.0 mg to 20 mg, 8.0 mg to 100 mg, 8.0 mg to 80 mg, 8.0 mg to 30 mg, 8.0 mg to 20 mg, 9.6 mg to 100 mg, 9.6 mg to 80 mg, 9.6 mg to 30 mg, 9.6 mg to 20 mg, 10 mg to 100 mg, 10 mg to 80 mg, 10 mg to 30 mg, 10 mg to 20 mg, 1.0 mg to 10 mg, 1.0 mg to 9.6 mg, 1.0 mg to 8.0 mg, 1.0 mg to 6.0 mg, 2.0 mg to 10.0 mg, 2.0 mg to 9.6 mg. 2.0 mg to 8.0 mg, 2.0 mg to 6.0 mg, 2.0 mg to 24.0 mg, or 2.0 mg to 12 mg, based on semaglutide. The pharmaceutical composition according to the present invention comprising the microsphere comprising the semaglutide or pharmaceutically acceptable salt thereof according to the present invention may be administered by parenteral administration, for example, subcutaneous injection. The pharmaceutical composition according to the present invention may be administered using a pre-filled syringe, for example, a pen syringe, this pen syringe may be a disposable syringe comprising a single dose, or metered dose syringe (syringe with does metering device) injected by only a single dose upon administration.

As one specific embodiment, the sustained-release microsphere containing the semaglutide or pharmaceutically acceptable salt thereof comprised in the pharmaceutical composition according to the present invention has a high drug content compared to the content of the microsphere, and also inhibits the initial burst of drug which may cause fatal side effects and exhibits efficacy as a GLP-1 agonist enough for a desired period, and therefore, it is useful for prevention or treatment of diabetes, specifically, type 2 diabetes, beta-cell function preservation, high blood pressure, hyperlipidemia, obesity, non-alcoholic steatohepatitis, or neurodegenerative diseases such as Alzheimer's disease and Parkinson's disease.

As other one aspect, the present invention provides a method for preparing a sustained-release microsphere containing semaglutide or a pharmaceutically acceptable salt thereof.

Hereinafter, the method for preparation of a sustained-release microsphere injection agent containing the semaglutide or pharmaceutically acceptable salt thereof of the present invention is specifically described.

The sustained-release microsphere injection agent containing the semaglutide or pharmaceutically acceptable salt thereof according to the present invention may be prepared using for example, "solvent extraction and evaporation method", but the method for preparation is not limited thereto.

As one specific example of the method for preparation of a sustained-release microsphere containing the semaglutide or pharmaceutically acceptable salt thereof according to the present invention, this method for preparation comprises (a) dissolving semaglutide or a pharmaceutically acceptable salt thereof and biodegradable polymer in an organic solvent to prepare solution (dispersed phase) containing the semaglutide or a pharmaceutically acceptable salt thereof and the polymer;

(b) adding the solution containing the semaglutide or pharmaceutically acceptable salt thereof and the polymer prepared in the step (a) to an aqueous phase (continuous phase) containing a surfactant to prepare emulsion;

(c) extracting and evaporating the organic solvent from the dispersed phase in an emulsion state prepared in the step (b) to the continuous phase to form a microsphere; and (d) collecting the microsphere from the continuous phase of the step (c) to prepare a microsphere comprising semaglutide or pharmaceutically acceptable salt thereof In the preparation of the sustained-release microsphere containing the semaglutide or pharmaceutically acceptable salt thereof according to the present invention, in order to inhibit excessive release of the initial semaglutide or pharmaceutically acceptable salt thereof while comprising the semaglutide or pharmaceutically acceptable salt thereof in a high content compared to the weight of the microsphere, and be released at a certain concentration for a desired long period, for example, for 1 month or more, 3 months or more, 1 month to 2 months, 1 month to 3 months, 1 month to 4 months, 1 month to 5 months, 1 month to 6 months, 2 months to 6 months, 2 months to 5 months, 2 months to 4 months, 2 months to 3 months, 3 months to 5 months, or 3 months to 4 months, as biodegradable polymer, specifically, it is preferable to use one or more selected from the group consisting of a polymer selected from the group consisting of polylactide (PLA), polyglycolide (PGA), polylactide-co-glycolide (PLGA) which is a copolymer of lactide and glycolide, polyorthoester, polyanhydride, polyhydroxybutyric acid, polycaprolactone and polyalkylcarbonate, a copolymer or simple mixture of 2 or more thereof, a copolymer of the polymer and polyethyleneglycol (PEG), and a polymer-sugar complex which the polymer or copolymer is linked with sugar. As one specific embodiment, in the method for preparation according to the present invention, as biodegradable polymer, a poly(lactide-co-glycolide) and/or polylactide polymer may be used.

In the present invention, in case of comprising 2 or more polymers with different repeating units composing the polymers and 2 or more repeating units, the two or more biodegradable polymers different each other may comprise 2 or more polymers with different molar ratios of the repeating unit. In addition, the microsphere may be a mixture of a microsphere comprising poly-lactide-co-glycolide and a microsphere comprising a polylactide polymer, or a microsphere comprising poly-lactide-co-glycolide and polylactide polymers together. In case of comprising the 2 or more repeating units, the 2 or more polymers with different molar ratios of the repeating units may have for example, a molar ratio (lactide:glycolide) of the repeating unit of lactide and glycolide in the poly-lactide-co-glycolide of 50:50 to 100:0, 60:40 to 90:10, or 70:30 to 80:20.

As one specific example, when the biodegradable polymers different each other are 2 kinds, the content ratio of these biodegradable polymers may be 0.5:10 to 10:0.5, 0.5:8 to 8:0.5, 1:10 to 10:1, 1:4 to 4:1, 1:3 to 3:1 or 1:2 to 2:1 as a weight ratio, but not limited thereto.

As a more specific aspect, in order to make a sustained-release microsphere containing the semaglutide or pharmaceutically acceptable salt thereof according to the present invention, when poly lactide-co-glycolide is used as two or more biodegradable polymers, at least one or more biodegradable polymers with intrinsic viscosity of 0.25 dL/g to 0.44 dL/g may be comprised. More preferably, the molar ratio (lactide:glycolide) of the repeating unit of lactide and glycolide of the biodegradable polymer may be 95:5 to 50:50, 85:15 to 50:50, 75:25 to 50:50.

As a specific aspect, the sustained-release microsphere containing the semaglutide or pharmaceutically acceptable salt thereof according to the present invention may prepare a sustained-release microsphere comprising the semaglutide or pharmaceutically acceptable salt thereof comprising 2 or more polymers by dissolving the semaglutide or pharmaceutically acceptable salt thereof and 2 or more biodegradable polymers, for example, 2 or more polymers selected from the group consisting of poly(lactide-co-glycolide) and polylactide polymers in an organic solvent simultaneously in the step (a).

Moreover, the sustained-release microsphere containing the semaglutide or pharmaceutically acceptable salt thereof according to the present invention may be prepared by mixing 2 or more microspheres comprising semaglutide or a pharmaceutically acceptable salt thereof different each other, comprising polymers different each other prepared through the step (a) to the step (d) using 2 or more biodegradable polymers different each other, for example, poly (lactide-co-glycolide) or polylactide polymers. Specifically, such 2 or more microspheres containing semaglutide or a pharmaceutically acceptable salt different each other, comprising polymers different each other, may be prepared by a method for preparation comprising the following steps.

(a') dissolving semaglutide or a pharmaceutically acceptable salt thereof and one or more biodegradable polymers different each other in an organic solvent to prepare a solution (dispersed phase) containing the semaglutide or pharmaceutically acceptable salt thereof and the polymer;

(b') adding the solution containing the semaglutide or pharmaceutically acceptable salt thereof and the polymer prepared in the step (a') to an aqueous phase (continuous phase) containing a surfactant to prepare emulsion;

(c') extracting and evaporating the organic solvent from the dispersed phase in an emulsion state prepared in the step (b') to the continuous phase to form a microsphere; and (d') repeating a process for preparing a microsphere comprising collecting a microsphere from the continuous phase in the step (c') to prepare a microsphere 2 times or more to prepare 2 or more microspheres different each other, (e') mixing the 2 or more microspheres consisting of different kinds of polymers each other.

Otherwise, it may be prepared by a method for preparation comprising the following steps.

(a") dissolving semaglutide or a pharmaceutically acceptable salt thereof and 2 or more biodegradable polymers different each other in an organic solvent, respectively, to prepare 2 or more solutions (dispersed phase) containing the semaglutide or pharmaceutically acceptable salt thereof and the polymer;

(b") adding the 2 or more solutions containing the semaglutide or pharmaceutically acceptable salt thereof and polymer prepared in the step (a") to an aqueous phase (continuous phase) containing a surfactant, respectively, to prepare 2 or more emulsions;

(c") extracting and evaporating the organic solvent from the 2 or more the dispersed phase in an emulsion state prepared in the step (b") to the continuous phase, by putting the 2 or more dispersed phases in emulsion state prepared in the step (b') into the same reactor, to form microspheres; and (d") collecting microspheres from the continuous phase in the step (c").

In the step (a), (a') or (a"), the one or more biodegradable polymers may be poly(lactide-co-glycolide) or polylactide. The intrinsic viscosity of the poly(lactide-co-glycolide) or polylactide is preferably in a range of 0.16~1.7 dL/g.

In the step (a), (a') or (a"), the organic solvent used for dissolving the semaglutide or pharmaceutically acceptable salt thereof and one or more biodegradable polymers is one or more organic solvents. In addition, the organic solvent may use a mixed organic solvent in which one or more organic solvents are mixed. As one specific aspect, the mixed solvent may be a mixed solvent of an organic solvent to be mixed with water and an organic solvent not to be mixed with water. In this case, it is preferable to use at least 50% (v/v) or more the organic solvent with a property not to be mixed with water. By using the property not to be mixed with water of the organic solvent, in the step (b), (b') or (b") to be described later, emulsion may be formed by homogeneously mixing the dispersed phase in the continuous phase containing a surfactant. The kind of the organic solvent which dissolves this semaglutide or pharmaceutically acceptable salt thereof and one or more biodegradable polymers is not particularly limited, but preferably, a mixed solvent of one or more solvents selected from the group consisting of dichloromethane, chloroform, ethyl acetate, methyl ethyl ketone, acetone, acetonitrile, dimethylsulfoxide, dimethylformamide, N-methyl pyrrolidone, acetate, methyl alcohol, ethyl alcohol, propyl alcohol and benzyl alcohol, more preferably, one solvent selected from dichloromethane and ethyl acetate, and one or more organic solvents selected from dimethyl sulfoxide, N-methyl pyrrolidone, methyl alcohol and acetate may be used.

In the step (b), (b') or (b"), the method for homogeneously mixing a continuous phase containing the semaglutide or pharmaceutically acceptable salt thereof-polymer solution and a surfactant is not particularly limited, but it may be performed using a high-speed stirrer, an in-line mixer, a membrane emulsion method, a microfluidics emulsion method, an ultrasonic mixer or a static mixer, or the like. When emulsion is formed using a high-speed stirrer, an in-line mixer, an ultrasonic mixer or a static mixer, it is difficult to obtain uniform emulsion, between the step (c) and the step (d), between the step (c') and the step (d'), or between the step (c") and the step (d") described later, it is preferable to additionally perform a sieving process, and the like. Emulsion in a uniform size may be obtained when using the membrane emulsion method and microfluidics emulsion method, and therefore, a sieving process and the like is not additionally needed, between the step (c) and the step (d), between the step (c') and the step (d'), or between the step (c") and the step (d") described later, and thus, it is preferable.

The type of the surfactant used in the step (b), (b') or (b") is not particularly limited, any one may be used as long as it can help for the semaglutide or pharmaceutically acceptable salt thereof-polymer solution to form a dispersed phase of stable droplets within a continuous phase. As the surfactant, polyvinylalcohol may be used.

In the step (b), (b') or (b"), the content of the surfactant in the continuous phase containing the surfactant may be 0.01 w/v % to 20 w/v %, preferably, 0.03 w/v % to 18 w/v %, 0.05 w/v % to 15 w/v %, 0.07 w/v % to 10 w/v % or 0.1 w/v % to 5 w/v %, based on the total volume of the continuous phase comprising the surfactant. When the content of the surfactant is less than 0.01 w/v %, a dispersed phase or emulsion in a form of droplets in the continuous phase may not be formed, and when the content of the surfactant is over 20 w/v %, there may be a difficulty in removing the surfactant, after a microsphere is formed in the continuous phase due to the excessive amount of surfactant.

As the continuous phase used in the step (b), (b') or (b"), water may be used, and in order to control the extraction rate of the organic solvent from the dispersed phase in an emulsion state, water containing some of one or more selected from the group consisting of methyl alcohol, ethyl alcohol, propyl alcohol and ethyl acetate may be used.

In addition, the pH of the continuous phase may be 5 or less, 4 or less, 3 or less, 2 to 5, 2 to 4, 2 to 3 or 2.5 to 3, but not limited thereto. When the pH of the continuous phase is adjusted within the range, the H and ion concentrations are adjusted, and the initial release of the semaglutide or pharmaceutically acceptable salt thereof in the microsphere is adjusted, and thus, it may be much further lowered.

In the step (c), (c') or (c"), when the emulsion comprising a dispersed phase in a form of droplets and a continuous phase containing a surfactant is maintained or stirred at a temperature less than the boiling point of the organic solvent for a certain time, for example, 2 hours to 48 hours, the organic solvent may be extracted in a continuous phase from the semaglutide or pharmaceutically acceptable salt thereof-polymer solution in a form of droplets which are in a dispersed phase. Some of the organic solvent extracted in a continuous phase may be evaporated from the surface. As the organic solvent is extracted and evaporated from the semaglutide or pharmaceutically acceptable salt thereof- polymer solution in a form of droplets, the dispersed phase in a form of droplets may be solidified to form a microsphere.

In the step (c), (c') or (c"), in order to efficiently remove the organic solvent additionally, for the temperature of the continuous phase, heat may be applied for a certain time. The heating temperature is not limited, and those skilled in the art may be appropriately adjusted according to the organic solvent used. For example, when dichloromethane is used as the organic solvent, heat may be applied to maintain 30° C. or more, 40° C. or more, 45° C. or more, 30 to 50° C., 40 to 50° C., or 45° C.

In the step (d), (d') or (d"), the method for recovering the microsphere containing semaglutide or a pharmaceutically acceptable salt thereof may be performed using various known techniques, and for example, a method of filtration or centrifugation, or the like may be used.

Between the step (c) and the step (d), between the step (c') and the step (d'), or between the step (c") and the step (d"), a remaining surfactant may be removed by filtration and washing, and a microsphere may be recovered by filtration again.

The washing for removing the remaining surfactant may be performed commonly using water, and the washing may be repeated through several times.

Furthermore, as described above, when emulsion is formed using a high-speed stirrer or in-line mixer in the step (b), (b') or (b"), between (c) and (d), between the step (c') and (d'), or between the step (c") and (d"), a homogeneous microsphere may be obtained by additionally using a sieving process. The sieving process may be performed using a known technology, and microspheres in a uniform size may be obtained by filtering out microspheres of small and large particles using sieves with different sizes each other.

The method for preparation of the present invention, after the (d), (d') or (d") or after the filtering and washing, by drying the obtained microspheres using a common during method, dried microspheres may be finally obtained.

In addition to the aforementioned matters, for all matters including semaglutide, biodegradable polymer and their contents which are not defined separately, all matters defined in the pharmaceutical composition may be applied as they are.

According to the method for preparation of the present invention, a sustained-release microsphere injection agent containing semaglutide or a pharmaceutically acceptable salt thereof in which the semaglutide or pharmaceutically acceptable salt drug is maintained at an effective concentration for a desired period without rapid temporary release may be prepared. In addition, a sustained-release microsphere injection agent containing semaglutide or a pharmaceutically acceptable salt thereof of uniform particles with good administration capacity may be prepared.

Mode for Invention

EXAMPLE

Hereinafter, the present invention will be described in more detail by preparative examples below. However, the following preparative examples illustrate the present invention only, but the content of the present invention is not limited by the following examples.

Preparative Example

Examples 1-37 and Comparative Examples 1 to 4: Preparation of Biodegradable Polymer Microsphere Comprising Semaglutide or Pharmaceutically Acceptable Salt Thereof A dispersed phase was prepared by mixing one or more selected from PLGA or PLA (trade name: Resomer®, manufacturer: Evonik, Germany) as biodegradable polymer, and semaglutide (manufacturer: Chengdu, China) or a pharmaceutically acceptable salt thereof (manufacturer: G2GBIO, Korea) as a drug and a release controlling agent in a mixed solvent (about 1.7:1 weight ratio) of dichloromethane (manufacturer: J.T Baker, U.S.A) and glacial acetic acid (manufacturer: Daejeong, Korea). The dispersed phase was stirred for 30 minutes or more and dissolved sufficiently and used. For a continuous phase, 1% polyvinylalcohol (viscosity: 4.8-5.8 mPa·s) aqueous solution was used, and the continuous phase was supplied to an emulsifying equipment equipped with a porous membrane with a diameter of 20 μm and at the same time, the prepared dispersed phase was injected to prepare emulsion in which biodegradable polymer microdroplets comprising semaglutide were dispersed, and this emulsion was put in a preparation container and stirred at a speed of 200 rpm.

The temperature of the membrane emulsifying equipment and preparation container was maintained at 25° C., and when completing the injection of the dispersed phase, the organic solvent was removed while maintaining the temperature of the suspension of the composition according to the present invention at 45° C. for 3 hours. After finishing the removal of the organic solvent, the suspension temperature was lowered to 25° C. The suspension was repeatedly washed with ultrapure water several times to remove the remaining polyvinylalcohol and the obtained composition in a particle form was lyophilized.

TABLE 1

| | Polymer type (g) | Polymer amount (g) | Drug amount (g) | Amount of solvent for dispersed phase(g) | Amount of solvent for continuous phase (g) | Drug | Release controlling agent/input amount | pH of continuous phase |
|---|---|---|---|---|---|---|---|---|
| Example 01 | RG653H | 0.95 | 0.05 | 11.4 | 1440 | Semaglutide[a] | N/A | |
| Example 02 | RG753H | 0.9472 | 0.05 | 11.40 | 1080 | Semaglutide[a] | myristic acid/ 0.0028 g | |
| Example 03 | RG753H/ RG653H(1:1) | 0.57 | 0.03 | 6.86 | 648 | Semaglutide[a] | | |
| Example 04 | RG753H/ RG653H(1:1) | 0.555 | 0.045 | 7.72 | 730 | Semaglutide[a] | | |

TABLE 1-continued

| | Polymer type (g) | Polymer amount (g) | Drug amount (g) | Amount of solvent for dispersed phase(g) | Amount of solvent for continuous phase (g) | Drug | Release controlling agent/input amount | pH of continuous phase |
|---|---|---|---|---|---|---|---|---|
| Example 05 | RG653H/ RG753H(1:1) | 0.90 | 0.10 | 14.46 | 1350 | Semaglutide[a)] | N/A | |
| Example 06 | RG753H/ RG653H(1:1) | 1.3875 | 0.1125 | 19.30 | 1823 | Semaglutide[b)] | | |
| Example 07 | RG753H/ RG653H(1:1) | 1.85 | 0.15 | 25.70 | 2430 | Semaglutide[b)] | | pH 2.79/ 1% acetic acid |
| Example 08 | RG753H/ RG653H(1:1) | 1.3875 | 0.1125 | 19.30 | 1823 | Semaglutide[b)] | | pH 2.77/ 1.6 mM Hydrochloric acid |
| Example 09 | RG753H/ RG653H(1:1) | 1.3875 | 0.1125 | 19.30 | 1823 | Semaglutide[b)] | | pH 1.98/ 0.2M Citrate Buffer |
| Example 10 | RG753H/ RG653H(1:1) | 1.3875 | 0.1125 | 19.30 | 1823 | Semaglutide[b)] | | pH 2.98/ 0.2M Citrate Buffer |
| Example 11 | RG753H/ RG653H(1:1) | 1.3875 | 0.1125 | 19.30 | 1823 | Semaglutide[b)] | | pH 3.98/ 0.2M Citrate Buffer |
| Example 12 | RG753H/ RG653H(1:1) | 1.3875 | 0.1125 | 19.30 | 1823 | Semaglutide[b)] | | pH 4.98/ 0.2M Citrate Buffer |
| Example 13 | RG753H/ RG653H(1:1) | 1.3875 | 0.1125 | 19.30 | 1823 | Semaglutide[b)] | | pH 3.27/ 0.2M Acetate Buffer |
| Example 14 | RG753H/ RG653H(1:1) | 1.3875 | 0.1125 | 19.30 | 1823 | Semaglutide[b)] | | pH 2.98/ 0.2M Lactate Buffer |
| Example 15 | RG503H | 0.95 | 0.05 | 11.40 | 1080 | Semaglutide[a)] | N/A | |
| Example 16 | RG753H | 0.95 | 0.05 | 12.60 | 1200 | Semaglutide[a)] | N/A | |
| Example 17 | R203H | 0.95 | 0.05 | 11.40 | 1080 | Semaglutide[a)] | N/A | |
| Example 18 | RG753H | 0.9 | 0.1 | 14.25 | 1080 | Semaglutide[a)] | N/A | |
| Example 19 | RG753H | 0.85 | 0.15 | 17.10 | 1620 | Semaglutide[a)] | N/A | |
| Example 20 | RG753H | 0.9645 | 0.05 | 11.40 | 1080 | Semaglutide[a)] | Stearic acid/ 0.0035 g | |
| Example 21 | RG753H | 0.328 | 0.06 | 16.30 | 1350 | Semaglutide[a)] | Pamoic acid/ 0.012 g | |
| Example 22 | RG753H | 0.425 | 0.075 | 21.10 | 1750 | Semaglutide pamoate | N/A | |
| Example 23 | RG753H/ R203H(1:1) | 0.95 | 0.05 | 14.25 | 1080 | Semaglutide[a)] | N/A | |
| Example 24 | RG503H/ RG504H(1:1) | 0.90 | 0.10 | 14.25 | 1080 | Semaglutide[a)] | N/A | |
| Example 25 | R202H/ R205S(1:1) | 0.95 | 0.05 | 14.25 | 1280 | Semaglutide[a)] | N/A | |
| Example 26 | RG504H | 0.95 | 0.05 | 11.40 | 1080 | Semaglutide[a)] | N/A | |
| Example 27 | R205S | 0.95 | 0.05 | 11.40 | 1080 | Semaglutide[a)] | N/A | |
| Example 28 | RG858S | 0.95 | 0.05 | 14.25 | 1350 | Semaglutide[a)] | N/A | |
| Example 29 | PLGA-glucose | 0.45 | 0.05 | 21.10 | 1750 | Semaglutide[a)] | N/A | |
| Example 30 | RG753H/ RG653H(2:1) | 0.555 | 0.045 | 7.72 | 730 | Semaglutide[a)] | N/A | |
| Example 31 | RG753H/ RG653H(1:2) | 0.555 | 0.045 | 7.72 | 730 | Semaglutide[a)] | N/A | |
| Example 32 | RG753H/ RG503H(1:1) | 1.3875 | 0.1125 | 19.30 | 1823 | Semaglutide[b)] | N/A | |
| Example 33 | RG753H/ RG502H(2:1) | 1.3875 | 0.1125 | 19.30 | 1823 | Semaglutide[b)] | N/A | |
| Example 34 | RG753H/ RG502H(4:1) | 1.3875 | 0.1125 | 19.30 | 1823 | Semaglutide[b)] | N/A | |
| Example 35 | RG753H/ RG653H/ RG502H(2:2:1) | 1.3875 | 0.1125 | 19.30 | 1823 | Semaglutide[b)] | N/A | |
| Example 36 | RG753H/ RG653H/ RG503H(2:2:1) | 1.3875 | 0.1125 | 19.30 | 1823 | Semaglutide[b)] | N/A | |

TABLE 1-continued

| | Polymer type (g) | Polymer amount (g) | Drug amount (g) | Amount of solvent for dispersed phase(g) | Amount of solvent for continuous phase (g) | Drug | Release controlling agent/input amount | pH of continuous phase |
|---|---|---|---|---|---|---|---|---|
| Example 37 | RG753H/ RG653H/ RG504H(2:2:1) | 1.3875 | 0.1125 | 19.30 | 1823 | Semaglutide[b] | N/A | |
| Comparative example 01 | RG752H | 0.95 | 0.05 | 11.40 | 1080 | Semaglutide[a] | N/A | |
| Comparative example 02 | RG502H | 0.95 | 0.05 | 11.4 | 1080 | Semaglutide[a] | N/A | |
| Comparative example 03 | R202H | 0.95 | 0.05 | 11.4 | 1080 | Semaglutide[a] | N/A | |
| Comparative example 04 | RG753S | 0.95 | 0.05 | 11.4 | 1080 | Semaglutide[a] | | |

[a]semaglutide sodium salt
[b]semaglutide free base

Example 38 to Example 43: Preparation of Preparations Comprising 2 or More Microspheres Comprising Polymers Different Each Other Sustained-release microsphere preparations comprising the semaglutide or pharmaceutically acceptable salt prepared in Preparative examples above were called Examples 38 to 43 by mixing them as Table 2 below.

TABLE 2

| Classification | micro-sphere 1 | micro-sphere 2 | micro-sphere 3 | Mixing ratio | | |
|---|---|---|---|---|---|---|
| Example 38 | Example 16 | Comparative example 02 | — | 1 | 1 | — |
| Example 39 | Example 16 | Example 15 | — | 1 | 1 | — |
| Example 40 | Example 16 | Example 28 | — | 1 | 1 | — |
| Example 41 | Example 16 | Comparative example 03 | — | 1 | 1 | — |
| Example 42 | Example 01 | Example 16 | Comparative example 02 | 2 | 2 | 1 |
| Example 43 | Example 01 | Example 16 | Example 15 | 2 | 2 | 1 |

Experimental Example 1: Measurement of Encapsulated Amount of Semaglutide in Microspheres In order to measure the encapsulated amount of semaglutide of the microspheres prepared in Preparative example 1 to 19, the microsphere 6 mg was completely dissolved in DMSO, and then diluted with a mobile phase. The diluted solution 20 μL was injected into HPLC and it was measured at a detection wavelength 214 nm. The column utilized in the present experimental example was ZORBAX 300SB-C18, 5 um, 4.6×150 mm, and the mobile phase was used in 45% 0.1% TFA acetonitrile, 55% 0.1% TFA aqueous solution isocratic mode. The measured encapsulated amount was shown in Table 3 below.

TABLE 3

| formulation | Amount (% by weight) |
|---|---|
| Example 01 | 4.17 |
| Example 02 | 4.60 |
| Example 03 | 4.08 |
| Example 04 | 6.12 |
| Example 05 | 8.45 |
| Example 06 | 7.10 |

TABLE 3-continued

| formulation | Amount (% by weight) |
|---|---|
| Example 07 | 6.62 |
| Example 08 | 7.02 |
| Example 09 | 6.65 |
| Example 10 | 6.72 |
| Example 11 | 6.35 |
| Example 12 | 7.01 |
| Example 13 | 6.73 |
| Example 14 | 6.80 |
| Example 15 | 4.62 |
| Example 16 | 4.51 |
| Example 17 | 4.47 |
| Example 18 | 8.57 |
| Example 19 | 11.40 |
| Example 20 | 4.60 |
| Example 21 | 13.10 |
| Example 22 | 13.70 |
| Example 23 | 4.49 |
| Example 24 | 8.36 |
| Example 25 | 4.46 |
| Example 26 | 4.35 |
| Example 27 | 4.65 |
| Example 28 | 4.67 |
| Example 29 | 8.62 |
| Example 30 | 6.36 |
| Example 31 | 6.23 |
| Example 32 | 7.39 |
| Example 33 | 7.29 |
| Example 34 | 7.55 |
| Example 35 | 7.27 |
| Example 36 | 7.29 |
| Example 37 | 7.42 |
| Example 38 | 4.22 |
| Example 39 | 4.57 |
| Example 40 | 4.59 |
| Example 41 | 4.40 |
| Example 42 | 4.26 |
| Example 43 | 4.40 |
| Comparative example 01 | 3.93 |
| Comparative example 02 | 3.93 |
| Comparative example 03 | 4.28 |
| Comparative example 04 | 4.52 |

Experimental Example 2: Morphological Analysis of Microspheres by Electron Microscope In order to analyze morphological characteristics of the prepared microspheres, scanning electron microscope observation was conducted.

5 mg of the microsphere prepared according to Example 4 was placed on an aluminum stub with carbon tape, and platinum was coated using ION-COATER (COXEM, Korea). An aluminum stub was mounted on a scanning electron microscope (COXEM EM-30, Korea), and the morphological characteristics of the microsphere were observed with an acceleration voltage of 14 kV. FIG. 4 is an electron microscope photograph image of the sustained-release biodegradable polymer microsphere. As can be confirmed in FIG. 5, it could be confirmed that a perfectly spherical microsphere having a relatively uniform particle size was prepared, and the surface was smooth, and the particle size was uniform, despite of the use of acetic acid as a co-solvent for production of the microsphere in the present invention.

Experimental Example 3: Analysis of Microsphere Particle Size Using Laser Diffraction Method In order to quantitatively measure the average particle size, distribution and uniformity of the prepared microsphere, it was conducted. The experimental procedure was as follows.

The microsphere 50 mg was mixed with 1 mL ultrapure water and was mixed with a vortex mixer for 20 seconds, and then was put into an ultrasonic generator and dispersed for 1 minute. The microsphere dispersed solution was put into a particle size analysis device (Microtrac Bluewave, Japan) and it was measured for 20 seconds.

As an index of the particle size uniformity, the span value was obtained by Equation 1 as below.

$$Span\ Value = (Dv,0.9 - Dv,0.1)/Dv,0.5 \qquad \text{[Equation 1]}$$

TABLE 4

| Lot No. | Span | D50 |
|---|---|---|
| Example 01 | 0.50 | 23.77 |
| Example 02 | 0.53 | 22.36 |
| Example 04 | 0.64 | 24.10 |
| Example 06 | 0.77 | 24.62 |
| Example 08 | 0.92 | 23.84 |
| Example 15 | 0.75 | 22.53 |
| Example 16 | 0.63 | 24.84 |
| Example 18 | 0.71 | 20.41 |
| Example 19 | 0.57 | 21.34 |
| Example 20 | 0.52 | 25.54 |
| Example 26 | 0.59 | 21.63 |
| Comparative example 01 | 0.77 | 24.25 |
| Comparative example 02 | 0.73 | 22.40 |
| Comparative example 03 | 0.90 | 25.34 |
| Comparative example 04 | 0.56 | 23.60 |

Experimental Example 4: In-Vitro Initial Elution Test

In order to evaluate the drug delivery ability of the semaglutide sustained-release microsphere, a semaglutide elution test was conducted in vitro. The experimental procedure was as follows.

25 mg of the microsphere and 10 mM phosphate buffer solution (pH 7.4) 6 ml were put into an 8 ml HDPE bottle and stored in an incubator set at 37° C. At a predetermined time, 1 ml was taken, and centrifuged at 13000 rpm for 1 minute, and 0.5 ml of the supernatant was taken, and 20 µl was injected into HPLC. Then, the HPLC column and operating condition were same as the HPLC analysis condition of Experimental example 1. The result was shown in Table 5 below.

TABLE 5

| | in-vitro semaglutide cumulative release rate (%) | | | | | |
|---|---|---|---|---|---|---|
| | 0 hr | 1 hr | 3 hrs | 6 hrs | 12 hrs | 24 hrs |
| Example 01 | 0 | 1.60 | 1.70 | 1.80 | — | 2.20 |
| Example 02 | 0 | 0.70 | 0.90 | 1.00 | — | 1.00 |
| Example 03 | 0 | 0.50 | 0.70 | 0.90 | — | 1.20 |
| Example 04 | 0 | 0.80 | 1.10 | 1.30 | — | 1.50 |
| Example 05 | 0 | 2.90 | 3.30 | 3.70 | — | 3.90 |
| Example 06 | 0 | 0.30 | 0.50 | 0.60 | — | 0.80 |
| Example 07 | 0 | 0.00 | 0.00 | 0.00 | — | 0.40 |
| Example 08 | 0 | 0.40 | 0.60 | 0.80 | — | 1.40 |
| Example 09 | 0 | 0.27 | — | — | 0.41 | 0.55 |
| Example 10 | 0 | 0.27 | — | — | 0.40 | 0.53 |
| Example 11 | 0 | 0.29 | — | — | 0.41 | 0.53 |
| Example 12 | 0 | 0.28 | — | — | 0.41 | 0.54 |
| Example 13 | 0 | 0.29 | — | — | 0.42 | 0.55 |
| Example 14 | 0 | 0.28 | — | — | 0.43 | 0.58 |
| Example 15 | 0 | 1.20 | 1.40 | 1.50 | — | 2.00 |
| Example 16 | 0 | 1.60 | 1.70 | 1.80 | — | 2.20 |
| Example 18 | 0 | 2.30 | 2.70 | 3.00 | — | 3.00 |
| Example 19 | 0 | 45.50 | 47.60 | 50.00 | — | 51.60 |
| Example 20 | 0 | 1.20 | 1.50 | 1.70 | — | 1.70 |
| Example 26 | 0 | 3.60 | 3.80 | 3.80 | — | 4.20 |
| Example 30 | 0 | 0.00 | 1.20 | 1.40 | 1.70 | 1.80 |
| Example 31 | 0 | 0.00 | 1.00 | 1.30 | 1.60 | 1.80 |
| Example 32 | 0 | 0.00 | 0.32 | — | — | 0.84 |
| Example 33 | 0 | 0.00 | 0.58 | — | — | 1.69 |
| Example 34 | 0 | 0.00 | 0.28 | — | — | 0.72 |
| Example 35 | 0 | 0.00 | 0.3 | — | — | 0.73 |
| Example 36 | 0 | 0.00 | 0.26 | — | — | 0.62 |
| Example 37 | 0 | 0.00 | 0.26 | — | — | 0.65 |
| Example 38 | 0 | 0.00 | 2.15 | 2.30 | 2.40 | 2.90 |
| Example 39 | 0 | 0.00 | 1.40 | 1.55 | 1.65 | 2.10 |
| Example 40 | 0 | 0.00 | 1.60 | 1.70 | 1.80 | 2.20 |
| Example 41 | 0 | 0.00 | 1.70 | 1.95 | 2.10 | 2.85 |
| Example 42 | 0 | 0.00 | 1.82 | 1.94 | 2.04 | 2.48 |
| Example 43 | 0 | 0.00 | 1.52 | 1.64 | 1.74 | 2.16 |
| Comparative example 02 | 0 | 2.70 | 2.90 | 3.00 | — | 3.60 |
| Comparative example 03 | 0 | 2.20 | 2.90 | 3.10 | — | 3.20 |
| Comparative example 04 | 0 | 0.50 | 0.60 | 0.80 | — | 0.80 |

As could be confirmed from the result of Table 5 above, when the pH of the continuous phase was acidic, it could be confirmed that the initial release rate within 24 hours was as low as 1/2 compared to the microsphere prepared using the continuous phase having a relatively high pH of 5.6. In addition, as the result of the in vitro initial elution test of the microspheres of Examples 9 to 14 prepared by varying the pH of the continuous phase and composition of the buffer for pH adjustment in the preparation of the microsphere of Example 6, it was confirmed that the initial release rate within 24 hours was reduced to about 60% to 75% compared to the microsphere of Example 6 without adjusting pH.

Experimental Example 6: Pharmacokinetic Test in Vivo Using Rats

In order to evaluate the in vivo drug release aspect of the semaglutide sustained-release microsphere according to the present invention, the semaglutide concentration in blood was measured after administering it into rats.

The microsphere was counted so that the semaglutide dose was 12.0 mg/kg, and dispersed in 0.5 mL suspension, and then injected into SD rats (Sprague-Dawley Rat). 0.5 mL blood was collected at pre-planned times, and the semaglutide concentration in blood was measured using HPLC. The measured change in the drug concentration of semaglutide in blood was shown in FIG. 1, FIG. 2 and FIG. 4, and the cumulative release rate was shown in FIG. 3.

As could be confirmed in FIG. 1 above, in case of the microspheres comprising semaglutide prepared in Comparative examples 1 to 3 in the present invention, it could be confirmed that a significantly high plasma drug concentration immediately after administration was shown and then the release of the drug was finished within 2 to 3 weeks after administration, and it could be confirmed that the microsphere of Comparative example 4 showed almost no drug release for 2 months after the low initial release.

On the other hand, FIG. 2 above confirms the change in the drug concentration in plasma over time after administering the microspheres comprising semaglutide prepared in Example 1, Example 2 and Example 4 of the present invention into rats, and the microspheres prepared according to the composition of the polymer according to the example of the present invention showed relatively low initial release of the drug compared to the comparative example, and after that, it could be confirmed that the drug was continuously released for 1 month or more.

In addition, FIG. 4 above confirms the change in the drug concentration in plasma over time after administering the microspheres comprising semaglutide prepared in Example 4 and Example 6 to Example 8 of the present invention, and in case of Example 6, and Example 7 and Example 8 in which the pH of the continuous phase was adjusted in the preparation of the microsphere, the result of the significantly reduced initial release of the drug compared to Example 4 could be confirmed.

FIG. 3 above confirms the change in the cumulative release rate of the drug over time after administering the microspheres of Example 4 and Example 6 to Example 8 of the present invention, and it could be confirmed that the drug was continuously released for 5 weeks or more after administration in case of the microsphere prepared according to the composition of the polymer according to the example of the present invention. In addition, the result that the initial release rate was significantly low according to adjustment of pH of the continuous phase and the drug was continuously released up to 63 days after administration could be confirmed.

The invention claimed is:

1. A pharmaceutical composition for treatment of diabetes, type 2 diabetes, beta-cell function preservation, obesity, non-alcoholic steatohepatitis or neurodegenerative diseases, comprising a sustained-release microsphere containing semaglutide freebase and a biodegradable polymer, wherein the biodegradable polymer comprises two different types of polylactide-co-glycolide (PLGA) with different lactide: glycolide molar ratios and/or different intrinsic viscosities, wherein the lactide: glycolide molar ratios are from 75:25 to 50:50, wherein each of the two types of PLGA has an intrinsic viscosity of 0.16-0.44 dL/g, the intrinsic viscosity being measured at a concentration of 0.1% (w/v) in chloroform at 25° C. using an Ubbelohde viscometer, wherein the content ratio of said two different types of PLGA is from 1:2 to 2:1, wherein said two different types of PLGA are acid terminated, wherein the semaglutide freebase is comprised in 3-12% by weight as semaglutide, based on the total weight of the microsphere, wherein the semaglutide freebase is released from the sustained-release microsphere by less than 10% within 24 hours after administration, and wherein the sustained-release microsphere releases the semaglutide freebase for one month or more.

2. The pharmaceutical composition according to claim 1, wherein the sustained-release microsphere have a dose-normalized AUC of at least 90 (ng*day/mL)/(mg/kg) or more during the total drug release period after subcutaneous administration to a SD rat.

3. The pharmaceutical composition according to claim 1, wherein the average particle size of the microsphere containing the semaglutide freebase is 5 μm to 100 μm.

4. The pharmaceutical composition according to claim 1, wherein the span value of the microsphere containing the semaglutide freebase is 1.5 or less.

5. The pharmaceutical composition according to claim 1, wherein the weight of the microsphere containing the semaglutide freebase is 20 to 1000 mg.

6. The pharmaceutical composition according to claim 1, further comprising one or more release controlling agents selected from the group consisting of butyric acid, valeric acid, caproic acid, enantic acid, caprylic acid, pelargonic acid, capric acid, undecylic acid, lauric acid, tridecylic acid, myristic acid, pentadecylic acid, palmitic acid, heptadecylic acid, stearic acid, nonadecylic acid, arachidic acid, isocrotonic acid, oleic acid, elaidic acid, sorbic acid, linoleic acid, arachidonic acid, hydroxynaphthoic acid, napadisylic acid and pamoic acid.

* * * * *